United States Patent [19]

Sacco

[11] 4,309,995
[45] Jan. 12, 1982

[54] VAGINAL IRRIGATION APPARATUS

[76] Inventor: Susan M. Sacco, 2316 Leyden Ave., River Grove, Ill. 60171

[21] Appl. No.: 115,909

[22] Filed: Jan. 28, 1980

[51] Int. Cl.³ .............................................. A61M 3/00
[52] U.S. Cl. ...................................... 128/239; 128/251
[58] Field of Search .............. 128/239, 251, 227, 232, 128/261; 401/203, 204

[56] References Cited

U.S. PATENT DOCUMENTS

| | | | |
|---|---|---|---|
| 795,211 | 7/1905 | Fanning | 401/203 |
| 800,254 | 9/1905 | Willis | 401/204 |
| 3,010,454 | 11/1961 | Lucie et al. | 128/251 |
| 3,054,403 | 9/1962 | Baker | 128/232 |
| 3,473,068 | 10/1969 | Hendricks et al. | 313/109.5 |
| 3,508,546 | 4/1970 | Rogers et al. | 128/230 |
| 3,512,526 | 5/1970 | Fielding | 128/239 |
| 3,709,224 | 1/1973 | Fielding | 128/239 |
| 3,731,682 | 5/1973 | Fielding | 128/239 |
| 3,867,938 | 2/1975 | Radcliffe | 128/225 |
| 4,057,060 | 11/1977 | Roth | 128/232 |

*Primary Examiner*—John D. Yasko

[57] ABSTRACT

A vaginal irrigation apparatus including a wall mounted supply container for irrigating medicant, a transfer tube and a disposable probe that is constructed of a liquid dispersing foam. The disposable probe includes a rigid proximal fitting, releasably connectable to the transfer tube, bonded to a patient insertable probe portion constructed entirely of polyurethane. The polyurethane is open cellular to readily disperse medicant, and it has sufficient rigidity to be inserted into the patient without the assistance of any implement.

14 Claims, 5 Drawing Figures

VAGINAL IRRIGATION APPARATUS

BACKGROUND OF THE PRESENT INVENTION

Vaginal irrigation devices have gained wide use in cleansing and treating the female organs. Many of these have been adapted for home use by the women patient without the need for any supervision or assistance. One such system includes a flexible rubber container or bottle suspended above the woman that conveys the irrigating fluid by gravity through a flexible transfer hose and a rigid plastic vaginal probe. The probe is reusable and has a central opening therethrough that disperses the medicant through a plurality of small apertures in the sides of the probe. This system has the primary disadvantage that because it is reusable, it is far from bacteriostatic even when cleansed carefully after each use, thus subjecting the female to repeated infection. Another disadvantage is that because of the rigid construction of the probe there is frequently vaginal discomfort during insertion and use.

In an attempt to increase the patient comfort of vaginal irrigating probes, several probes have been designed in which the probe is covered with a soft cellular foam material that is both non-irritating to the human tissue and resilient. Examples of these probes are illustrated in the Fielding U.S. Pat. Nos. 3,709,224 and 3,731,682. In the Fielding U.S. Pat. No. 3,731,682, a vaginal irrigating probe is illustrated having a soft cushioned body constructed of a sponge material, but because of the pliability of the body, it must be inserted with a rigid implement. This system also requires a rigid douche nozzle that is inserted into the cushioned body, after removal of the inserting implement, prior to irrigation. This system has not gained any considerable commercial acceptance, not only because of the expense of providing three separate parts, namely the cushioned body, the inserting element, and the rigid douche nozzle, but also because the apparatus is too difficult for the female to use with any facile.

The Fielding U.S. Pat. No. 3,709,224 shows a similar system to that shown in his U.S. Pat. No. 3,731,682, except that a rigid element used in insertion of the soft cushioned body remains implanted during irrigation. This arrangement has the same disadvantage as the device shown in his latter patent.

It is a primary object of the present invention to ameliorate the problems noted above in patient implanted irrigating devices and particularly vaginal irrigating devices.

SUMMARY OF THE PRESENT INVENTION

In accordance with the present invention, a vaginal irrigation apparatus is provided including a wall mounted medicant supply container, a transfer tube, and a disposable vaginal probe having an insertable portion constructed entirely from an open cellular foam such as polyurethane. Since the probe is disposable in its entirety, the bacteriology of the irrigating apparatus is vastly greater than any known vaginal irrigation system. While of course any vaginal probe may be disposed of after each use and replaced with another, the low material and manufacturing cost of the present disposable probe is significantly below commercially available probes and enable it to be competitive with existing irrigating apparatus even with repeated replacement.

The disposable probe consists of an external or proximal rigid plastic fitting that is selectively connected to the fluid transfer tube just prior to use. An elongated vaginally insertable probe portion constructed entirely of polyurethane is bonded to this fitting and has a central bore that receives the irrigating liquid or medicant and conveys it to the open cellular structure of the polyurethane. The polyurethane has a sufficiently low number of pores per inch, i.e. below eighty pores per inch, so that it readily disperses liquid medicant from its central bore or opening to the vagina with only the pressure produced by gravity feed from the supply container.

An important aspect of the present invention is that the probe may be inserted without the need for any separate rigid inserting implement and also requires no separate dispensing nozzle. Toward this end, the polyurethane probe portion has Indentation Load Deflection characteristic, i.e. ILD, in excess of (38) thirty-eight. This Indentation Load Deflection characteristic has several meanings in the plastic industry, but is frequently defined as the load in pounds required to deflect a specimen dimensioned 15"×15"33 4" twenty-five percent of its height. The same parameter or characteristic is sometimes referred to as "Compression Resistance" at twenty-five percent deflection in pounds per square inch. Using this parameter the compression resistance required is at least (5) five lbs. per square inch. To achieve this degree of rigidity the polyurethane used has additional cross-linking, when compared to the so called "flexible" polyurethanes and has a density in the range of four to six pounds per cubic foot. While a rigid polyurethane foam would be operable, it would not provide the same user comfort as the semi-flexible polyurethane foam described above. As is well known in the industry, polyester resins are generally reacted with various available diisocyanates to produce polyurethane foam employing a blowing agent such as carbon dioxide to effect the cellular foam structure.

Another important aspect of the present invention is the provision of a supply container that is removably mounted to a permanently installed wall bracket. The supply container can remain mounted in the bracket even when the apparatus is not in use, and the supply or transfer tube and additional probes may be stored in the supply container.

The wall bracket is designed to be mounted in the corner of the user's washroom and has a shelf that receives and holds the generally triangularly shaped supply container that has integrally formed recessed portions that provide a hand grip for easy removal of the container from the bracket.

The present vaginal irrigation apparatus has the primary advantage that it is almost completely bacteriostatic because of the disposable probes. It also produces significantly less patient discomfort because of the resiliency and porosity of the polyurethane portion of the probe. Because of the simplicity of construction and low cost of materials of the probe, it now becomes commercially possible to provide a disposable probe without significantly increasing the cost of the total vaginal irrigation system including use costs as well as initial costs.

DETAILED DESCRIPTION OF THE PREFERRED EMBODIMENT

Figures 1, 2:
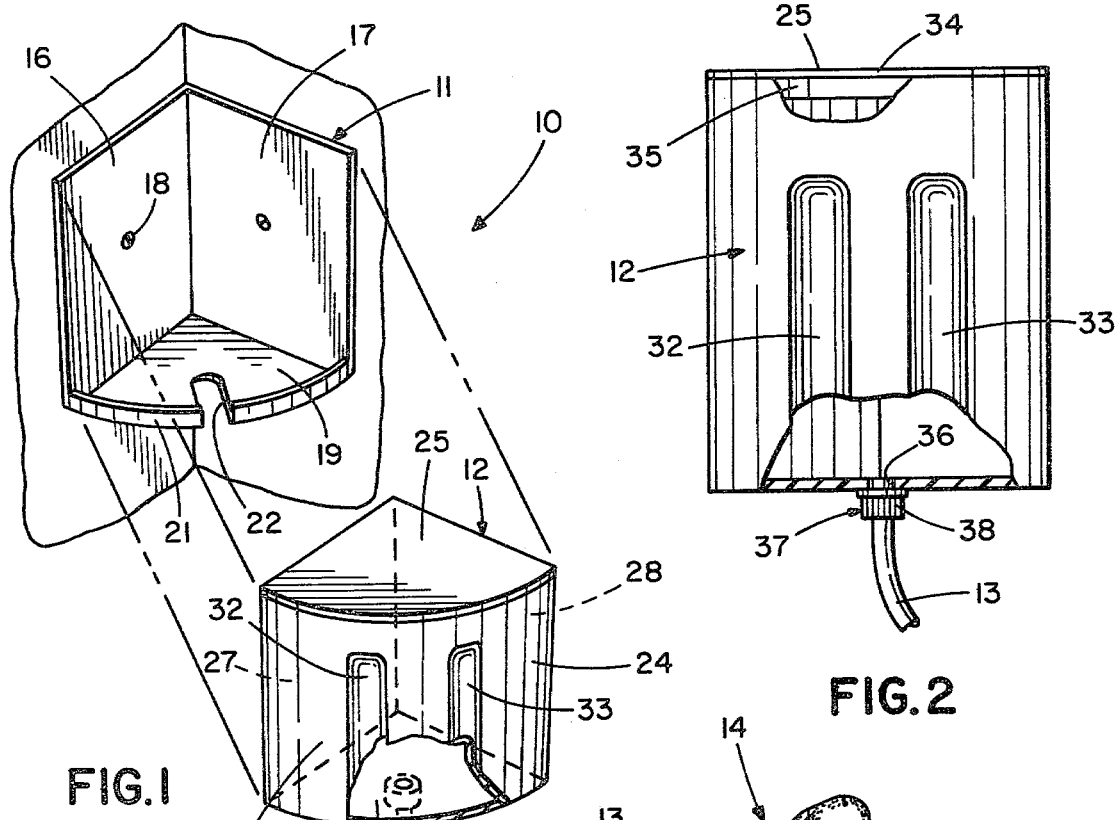
FIG. 1 is a perspective view of the present vaginal irrigation system.
FIG. 2 is a plan view, partly fragmentary of the irrigating fluid supply container.

Referring to the drawings and particularly FIG. 1, the present vaginal irrigation apparatus 10 is seen to generally include a bracket 11 that receives and supports a medicant container or reservoir 12 that supplies medicant or an irrigating liquid to the user through a transfer tube 13 and a vaginally insertable disposable probe 14. While the present invention is illustrated as a vaginal irrigating apparatus, it should be understood that the principles of the invention could apply to other medicant dispensing systems such as intestinal irrigators or medicant applicators that employ rectally insertable probes or nozzles.

The bracket 11 is a one-piece plastic molding constructed of a rigid durable plastic such as "Delran". Bracket 11 has perpendicular side panels 16 and 17 each of which has apertures for receiving fasteners 18 that fix the bracket 11 to the wall. An integral bottom wall 19 is provided joining the perpendicular side walls 16 and 17 and it has an arcuate forward lip 21 that engages the front of the container 12 to hold it securely in position. The bottom wall 19 and front lip 20 have a central recess or slot 22 therethrough that permits the transfer tube 13 to project downwardly through the bottom wall 19 permitting the container 12 to remain in the bracket 11 when the apparatus is being used. The bracket 11 is mounted on the wall well above the user so that the vaginal irrigation proceeds by gravity alone without the need for any pressurizing device.

The container 12 includes a one-piece body member 24 and a lid 25 both generally rectangular in configuration and also constructed of a rigid durable plastic material such as Delran. The container 12 includes perpendicular back surfaces 27 and 28 joined by a generally triangularly shaped integral bottom wall 29 and an arcuate front wall 30 that is congruent with the lip 21 on the bracket 11. The front wall 30 is provided with two parallel integrally formed vertical recesses 32 and 33 that define finger and thumb holes for the simple removal and insertion of the container 12 relative to the bracket 11.

As seen in FIG. 2, the lid 25 is removable from the container 12 and includes a top wall 34 coextensive with the outer periphery of the container 12 and a depending integral flange 35 that fits snugly within the interior surfaces of side walls 27 and 28 and front wall 30. In addition to providing a reservoir for medicant or irrigating liquid, the container 12 may also serve as a storage location for the transfer tube 13 and additional packaged disposable probes 14.

As seen in FIG. 2, the transfer tube 13 is connected to a central opening 36 formed centrally in the bottom wall 29 of the container 12 by a valve fitting 37. Valve fitting 37 is conventional in construction and serves not only to fix tube 13 to the container, but also selectively blocks flow from the container into the transfer tube 13 by the manual rotation of a sleeve portion 38 of the fitting.

Figure 3:
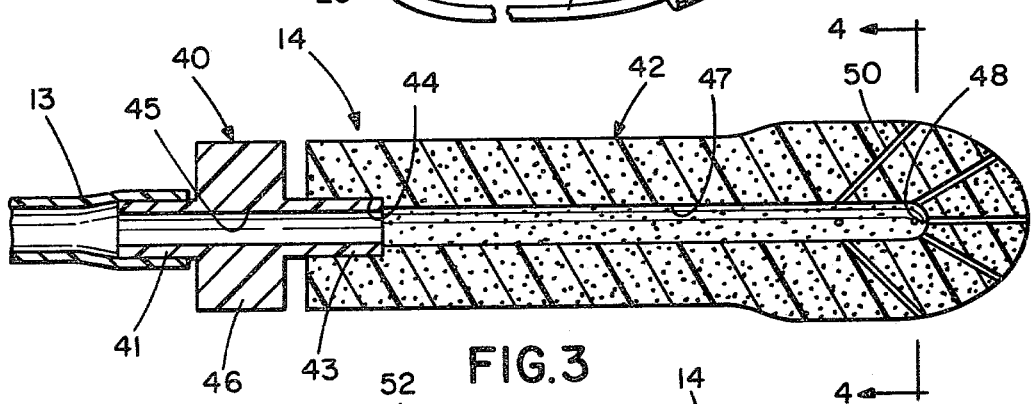
FIG. 3 is a cross-section of the disposable probe according to the present invention.
Figures 4, 5:
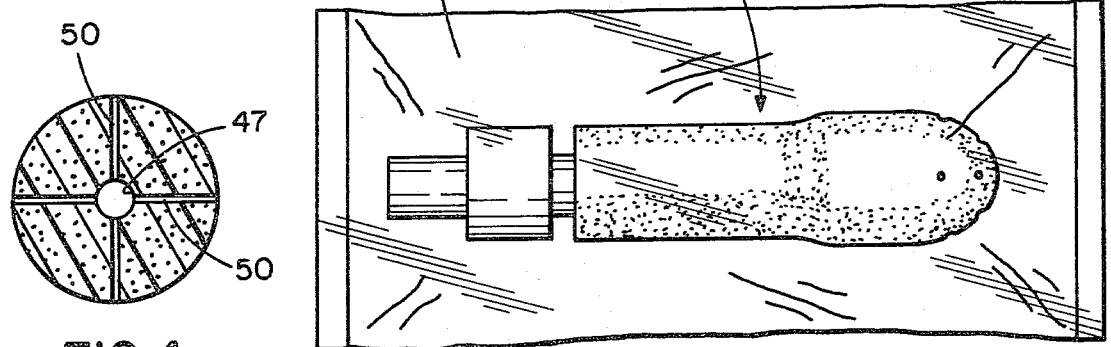
FIG. 4 is a cross-section taken generally along line 4—4 of FIG. 3.
FIG. 5 is a plan view of a disposable probe wrapped in its own container.

As seen in FIGS. 3, 4 and 5, the disposable probe 14 includes an annular plastic fitting 40 bonded to a polyurethane probe portion 42 that is insertable into the user's vagina.

The fitting 40 is constructed of a rigid plastic material such as a polycarbonate and is generally annular in configuration including a reduced inlet stem 41, an enlarged central portion 46 and a reduced outlet stem 43 bonded within a counterbore 44 in probe portion 42. A throughbore 45 extends completely through fitting 40, and the outer diameter of the inlet fitting 41 is sized somewhat greater than the inner diameter of the transfer tube 13 so that it forcibly receives the end of the transfer tube and holds it sealingly in position during use while at the same time permitting the ready release and re-attachment of the transfer tube during each use.

The vaginally insertable probe portion 42 has sufficient stiffness or rigidity so that the user may easily insert the probe portion into her vagina by merely grasping with her fingers the rigid fitting 42 and part of the left end of the probe portion 42 shown in FIG. 3. Toward this end, the probe portion 42 is constructed of a polyurethane foam having an Indentation Load Deflection characteristic greater than 40. The Indentation Load Deflection characteristic, referred to as in parts of the plastic industry as ILD, is the load in pounds required to deflect a $15'' \times 15'' \times 4''$ specimen of the foam material twenty-five percent. (Seen Encyclopedia of Chemical Technology" 2nd Edition, John Wiley and Sons, Inc. 1966.) It is possible to use a polyurethane material for probe portion 42 having an ILD significantly greater than forty, but as the probe portion material approaches the range of rigid polyurethane foams, the user comfort decreases. This additional rigidity or high ILD factor is obtained, as will appear to those skilled in the art, through the provision of additional cross-linking in the reaction forming the polyurethane which usually consists of reacting polyester resins with various diisocyanates with the addition of a blowing agent such as carbon dioxide.

The firmness of the polyurethane required may also be defined in terms of its compression resistance at twenty-five percent deflection in pounds per square inch. This parameter is also in extensive use as a load deflection parameter. Using this parameter, the present polyurethane probe 42 should have a compression resistance of at least (4) four PSI.

The porosity and density of the polyurethane probe portion 42 is selected to achieve not only the desired firmness for the probe 42 but also to provide the liberal flow of irrigating fluid throughout the length of the probe under only the force of gravity provided by the suspended supply container 12. An increase in the number of cells in the polyurethane, commonly referred to as pores per inch generally increases user comfort, while at the same time it increases probe density, but this has the effect of decreasing the probe's capability of liberally passing medicant. The balancing of these parameters is therefore important, and a probe porosity of (40) forty to (80) eighty pores per inch satisfies both adequate medicant dispersion without sacrificing user comfort significantly.

The probe portion 42 has a central opening 47 having a closed end 48 that freely communicates with the interior of the bore 45 of fitting 40 and extends throughout substantially the entire length of the polyurethane probe 42. The opening 47 is manufactured by a suitable cutting tool as is the entire probe portion 42. If desired, a plurality of radiating bores 50 may be cut through the probe portion 42 communicating bore 47 with the exterior surface of the probe portion, and these serve to provide greater flow of medicant to a particular area of the probe. The bores 50 should be sized relatively small relative to the pore size of the polyurethane materials selected to assure that medicant will flow outwardly from the bore 47 throughout the length of the probe portion and not simply through the bores 50.

As seen in FIG. 5, probe 14 is disposable in its entirety and they are individually packaged and sealed in a suitable packaging container 52 to maintain the probe's sterility until just prior to use. During use a new probe 14 is removed from container 52 and inserted into the distal end of the transfer tube 13. The distal end of probe portion 42 is then vaginally inserted and the valve sleeve 38 rotated to supply medicant or irrigating liquid to the user's vagina under the influence of gravity. After irrigation, probe 14 is removed, disconnected from transfer tube 13 and discarded.

What is claimed is:

1. A therapeutic irrigating apparatus for delivering medicant to the user through a rectally or vaginally implanted probe, comprising; a supply container for medicant, a transfer tube connected to and communicating with the supply container, and a disposable probe connected to the transfer tube for insertion into the patient, said probe being constructed of a semi-flexible or substantially rigid foam material that is unsupported throughout a major portion of its length and open cellular in structure to transfer medicant from the transfer tube to the patient, said foam having sufficent rigidity so that the unsupported probe may be rectally or vaginally inserted manually without any additional implements.

2. A therapeutic irrigating apparatus for delivering medicant to the user through a rectally or vaginally implanted probe, as defined in claim 1, wherein the probe is constructed of polyurethane.

3. A therapeutic irrigating apparatus for delivering medicant to the user through a rectally or vaginally implanted probe, as defined in claim 2, wherein said polyurethane has a density in the range of four to six pounds per square inch.

4. A therapeutic irrigating apparatus for delivering medicant to the user through a rectally or vaginally implanted probe, as defined in claim 2, wherein the polyurethane probe has an Indentation Load Deflection characteristic of at least forty.

5. A therapeutic irrigating apparatus for delivering medicant to the user through a rectally or vaginally implanted probe, comprising; a supply container for medicant, a transfer tube connected to and communicating with the supply container, and a plurality of disposable probes selectively connectable to the transfer tube for insertion into the patient or user, said probes having a user insertable portion constructed entirely of polyurethane material, said polyurethane material being open cellular and semi-flexible or rigid to permit the easy insertion of the probe into the user and the dispersion of medicant from the transfer tube to the patient through the cellular structure of the polyurethane, said polyurethane probe being unsupported throughout a major portion of its length and having sufficient rigidity so that the unsupported probe may be rectally or vaginally inserted manually without any additional implements.

6. A therapeutic irrigating apparatus for delivering medicant to the user through a rectally or vaginally implanted probe, as defined in claim 5, wherein each of the probes is enclosed in a separate container.

7. A therapeutic irrigating apparatus for delivering medicant to the user through a rectally or vaginally implanted probe, as defined in claim 5, wherein the polyurethane material has an Indentation Load Deflection characteristic above forty.

8. A therapeutic irrigating apparatus for delivering medicant to the user through a rectally or vaginally implanted probe, as defined in claim 5, wherein the polyurethane material has a density in the range of four to six pounds per cubic foot.

9. A therapeutic irrigating apparatus for delivering medicant to the user through a rectally or vaginally implanted probe, as defined in claim 5, wherein the polyurethane material has a compression resistance of at least 3 psi at twenty-five percent deflection.

10. A therapeutic irrigating apparatus for delivering medicant to the user through a rectally or vaginally implanted probe, as defined in claim 1, wherein the probe has a patient or user insertable portion constructed entirely of polyurethane, said probe having a fitting at the proximal end thereof connectable to the transfer tube, said insertable portion having a central opening extending a substantial distance therethrough and communicating with the fitting.

11. A disposable rectally or vaginally insertable probe for conveying irrigating medicant from a source to the user, comprising; a fitting adapted to be connected to a medicant supply tube, and a patient or user insertable probe portion connected to the fitting, said probe portion being constructed entirely of polyurethane and having a central opening communicating with the fitting, said polyurethane being unsupported throughout a major portion of its length and having sufficient rigidity so that the probe portion may be rectally or vaginally inserted manually without the need for any special implement.

12. A disposable rectally or vaginally insertable probe for conveying irrigating medicant from a source to the user, as defined in claim 11, wherein the polyurethane has a compression resistance at twenty-five percent material deflection of at least 4 psi.

13. A therapeutic irrigating apparatus for delivering medicant to the user through a rectally or vaginally implanted probe, comprising; a supply container for medicant, a transfer tube connected to and communicating with the supply container, and a disposable probe connected to the transfer tube for insertion into the patient, said probe being constructed of a semi-flexible or substantially rigid foam material that is unsupported throughout a major portion of its length and open cellular in structure to transfer medicant from the transfer tube to the patient, said foam having an Indentation Load Deflection characteristic as defined of approximately thirty so that the probe may be rectally or vaginally inserted without the need for a special implement.

14. A therapeutic irrigating apparatus for delivering medicant to the user through a rectally or vaginally implanted probe, comprising; a supply container for medicant, a transfer tube connected to and communicating with the supply container, and a disposable probe connected to the transfer tube for insertion into the patient, said probe being constructed of a semi-flexible or substantially rigid foam material that is unsupported throughout a major portion of its length and open cellular in structure to transfer medicant from the transfer tube to the patient, said foam having a compression resistance as defined at 25 percent of approximately 3 psi.

* * * * *